United States Patent
Lamoureux

(10) Patent No.: US 7,211,039 B2
(45) Date of Patent: May 1, 2007

(54) STRAND WITH END PLUG

(75) Inventor: Gary A. Lamoureux, Woodbury, CT (US)

(73) Assignee: Worldwide Medical Technologies LLC, Oxford, CT (US)

( * ) Notice: Subject to any disclaimer, the term of this patent is extended or adjusted under 35 U.S.C. 154(b) by 0 days.

(21) Appl. No.: 11/409,805

(22) Filed: Apr. 24, 2006

(65) Prior Publication Data

US 2006/0264688 A1    Nov. 23, 2006

Related U.S. Application Data

(60) Division of application No. 10/397,940, filed on Mar. 26, 2003, which is a continuation of application No. 10/035,083, filed on Dec. 28, 2001, now Pat. No. 7,060,020.

(60) Provisional application No. 60/336,329, filed on Nov. 2, 2001.

(51) Int. Cl.
    *A61N 5/00*    (2006.01)

(52) U.S. Cl. .......................................................... 600/3

(58) Field of Classification Search .................. 600/1–8
    See application file for complete search history.

(56) References Cited

U.S. PATENT DOCUMENTS

| | | |
|---|---|---|
| 1,578,945 A | 3/1926 | Withers |
| 2,067,589 A | 1/1937 | Antrim |
| 2,575,138 A | 11/1951 | Slaughter |
| 3,351,049 A | 11/1967 | Lawrence |
| 3,565,869 A | 2/1971 | De Prospero ............... 260/78.3 |
| 3,636,956 A | 1/1972 | Schneider ................ 128/335.5 |
| 3,752,630 A | 8/1973 | Takagi ........................ 425/325 |
| 3,811,426 A | 5/1974 | Culver et al. ................ 128/1.2 |
| 3,936,414 A | 2/1976 | Wright et al. ................ 523/517 |
| 4,052,988 A | 10/1977 | Doddi ...................... 128/335.5 |
| 4,086,914 A | 5/1978 | Moore ......................... 128/1.2 |
| 4,167,179 A | 9/1979 | Kirsch ......................... 128/1.2 |
| 4,402,308 A | 9/1983 | Scott ........................... 128/1.2 |
| 4,416,659 A | 11/1983 | Simpson et al. ............... 604/48 |
| 4,509,506 A | 4/1985 | Windorski et al. ........... 128/1.2 |

(Continued)

FOREIGN PATENT DOCUMENTS

| | | |
|---|---|---|
| EP | 0 030 822 B1 | 9/1983 |
| EP | 0 466 681 B1 | 1/1992 |
| WO | WO 00/64538 | 2/2000 |
| WO | WO 00/61229 | 10/2000 |

OTHER PUBLICATIONS

Webster's II New Riverside University Dictionary, 1984, p. 634.*

(Continued)

*Primary Examiner*—John P. Lacyk
(74) *Attorney, Agent, or Firm*—Fliesler Meyer LLP

(57) ABSTRACT

A treatment strand for insertion into a patient using a needle. The strand includes an elongated member having first and second longitudinal ends, and a plurality of treatments seeds spaced apart from one another within the elongated member between the longitudinal ends. A needle plug is located at one of the longitudinal ends of the elongated member and integrally formed with the elongated member. The integrally formed needle plug is configured to prevent at least one of fluid and tissue from entering a needle when the elongated member is loaded into a needle and the needle is initially inserted into a patient.

19 Claims, 1 Drawing Sheet

U.S. PATENT DOCUMENTS

| | | | | |
|---|---|---|---|---|
| 4,697,575 | A | 10/1987 | Horowitz | 128/1.2 |
| 4,754,745 | A | 7/1988 | Horowitz | 128/1.2 |
| 4,784,116 | A | 11/1988 | Russel, Jr. et al. | 128/1.2 |
| 4,815,449 | A | 3/1989 | Horowitz | 600/7 |
| 4,936,823 | A | 6/1990 | Colvin et al. | 600/7 |
| 4,946,435 | A | 8/1990 | Suthanthiran et al. | 600/3 |
| 5,022,940 | A | 6/1991 | Mehoudar | 156/64 |
| 5,339,812 | A | 8/1994 | Hardy et al. | 128/653.1 |
| 5,460,592 | A | 10/1995 | Langton et al. | 600/7 |
| 5,713,828 | A | 2/1998 | Coniglione | 600/7 |
| 5,761,877 | A | 6/1998 | Quandt | 53/155 |
| 5,833,593 | A | 11/1998 | Liprie | 600/3 |
| 5,928,130 | A | 7/1999 | Schmidt | 600/7 |
| 5,938,583 | A | 8/1999 | Grimm | 600/7 |
| 6,010,446 | A | 1/2000 | Grimm | 600/3 |
| 6,039,684 | A | 3/2000 | Ildstad et al. | 600/1 |
| 6,080,099 | A | 6/2000 | Slater et al. | 600/8 |
| 6,099,457 | A | 8/2000 | Good | 600/8 |
| 6,132,677 | A | 10/2000 | Ohriner | 419/67 |
| 6,132,947 | A | 10/2000 | Honan et al. | 430/546 |
| 6,159,143 | A | 12/2000 | Lennox | 600/4 |
| 6,163,947 | A | 12/2000 | Coniglione | 29/458 |
| 6,200,255 | B1 | 3/2001 | Yu | 600/1 |
| 6,200,256 | B1 | 3/2001 | Weinberger | 600/3 |
| 6,248,057 | B1 | 6/2001 | Mavity et al. | 600/3 |
| 6,264,599 | B1 | 7/2001 | Slater et al. | 600/7 |
| 6,264,600 | B1 | 7/2001 | Grimm | 600/7 |
| 6,273,851 | B1 | 8/2001 | Slater et al. | 600/8 |
| 6,283,911 | B1 | 9/2001 | Keren | 600/3 |
| 6,312,374 | B1 | 11/2001 | von Hoffmann | 600/3 |
| 6,327,490 | B1 | 12/2001 | Spetz | 600/427 |
| 6,360,116 | B1 | 3/2002 | Jackson, Jr. et al. | 600/427 |
| 6,387,034 | B1 | 5/2002 | Lee | 600/427 |
| 6,398,709 | B1 | 6/2002 | Ehr et al. | 600/3 |
| 6,403,916 | B1 | 6/2002 | Spooner et al. | 219/121.63 |
| 6,428,504 | B1 | 8/2002 | Riaziat et al. | 604/65 |
| 6,438,401 | B1 | 8/2002 | Cheng et al. | 600/407 |
| 6,450,937 | B1 | 9/2002 | Mercereau et al. | 600/7 |
| 6,450,938 | B1 | 9/2002 | Miller | 600/7 |
| 6,450,939 | B1 | 9/2002 | Grimm | 600/8 |
| 6,474,535 | B1 | 11/2002 | Shanks et al. | 228/164 |
| 6,497,646 | B1 | 12/2002 | Candelaria et al. | 600/7 |
| 6,500,109 | B2 | 12/2002 | Tokita et al. | 600/7 |
| 6,514,193 | B2 | 2/2003 | Kaplan | 600/7 |
| 6,537,193 | B1 | 3/2003 | Lennox | 600/3 |
| 6,539,247 | B2 | 3/2003 | Spetz | 600/427 |
| 6,549,802 | B2 | 4/2003 | Thornton | 600/426 |
| 6,572,525 | B1 | 6/2003 | Yoshizumi | 600/7 |
| 6,575,888 | B2 | 6/2003 | Zamora et al. | 600/3 |
| 6,595,908 | B2 | 7/2003 | Loffler et al. | 600/7 |
| 6,626,817 | B2 | 9/2003 | Luth | 600/7 |
| 6,632,176 | B2 | 10/2003 | McIntire et al. | 600/439 |
| 6,656,106 | B2 | 12/2003 | Schmidt | 600/7 |
| 6,709,381 | B2 | 3/2004 | Munro, III | 600/3 |
| 6,746,661 | B2 | 6/2004 | Kaplan | 424/1.25 |
| 6,752,753 | B1 | 6/2004 | Hoskins et al. | 600/7 |
| 6,761,680 | B2 | 7/2004 | Terwilliger et al. | 600/8 |
| 6,786,858 | B2 | 9/2004 | Terwilliger et al. | 600/3 |
| 6,820,318 | B2 | 11/2004 | Terwilliger et al. | 29/458 |
| 7,008,367 | B2 * | 3/2006 | Visscher et al. | 600/8 |
| 2003/0084988 | A1 | 5/2003 | Terwilliger et al. | |
| 2003/0092958 | A1 | 5/2003 | Terwilliger et al. | |
| 2003/0191355 | A1 | 10/2003 | Ferguson | |
| 2004/0158117 | A1 | 8/2004 | Drobnik et al. | |
| 2004/0158118 | A1 | 8/2004 | Drobnik et al. | |

OTHER PUBLICATIONS

Alvaro Martinez, et al; "Sterilization of $^{125}$I Seeds Encased in Vicryl Sutures for Permanent Interstitial Implantation"; Intl. J. Radiation Oncology Biol. Phys. vol. 5, pp. 411-413; Pergamen Press Ltd., 1979.

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm, "Mentor Acquires Breakthrough Brachytherapy Technology" (Jan. 25, 2002).

Medi-Physics brochure entitled I-215 Seeds. No. 6711, Medi-Physics, Inc. Arlington Heights II. 60004, USA; Revised. Oct. 1999, 2 pages.

Medi-Physics brochure entitled I-125 Seeds. No. 7000; Medi-Physics, Inc. Arlington Heights II. 60004, USA; Revised. Oct. 1999, 2 pages.

Amersham Health; "EchoSeed™"; http://www.amershamhealth-us.com/echoseed/ printed Nov. 19, 2003.

Amersham Health; "Rapid Strand Indications" Http;//www.amershamhealth-us.com/products/index.htp?a=i&i=38; printed Nov. 19, 2003.

Amersham Health; OncoSeed™ (Iodine-125 Seeds) http://www.amershamhealty-us.com/oncoseed/: printed Nov. 19, 2003.

RadioMed: Innovative Products for Radiation, "The Visicoil Advantage . . . for Image Guided Radiation Therapy," http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

* cited by examiner

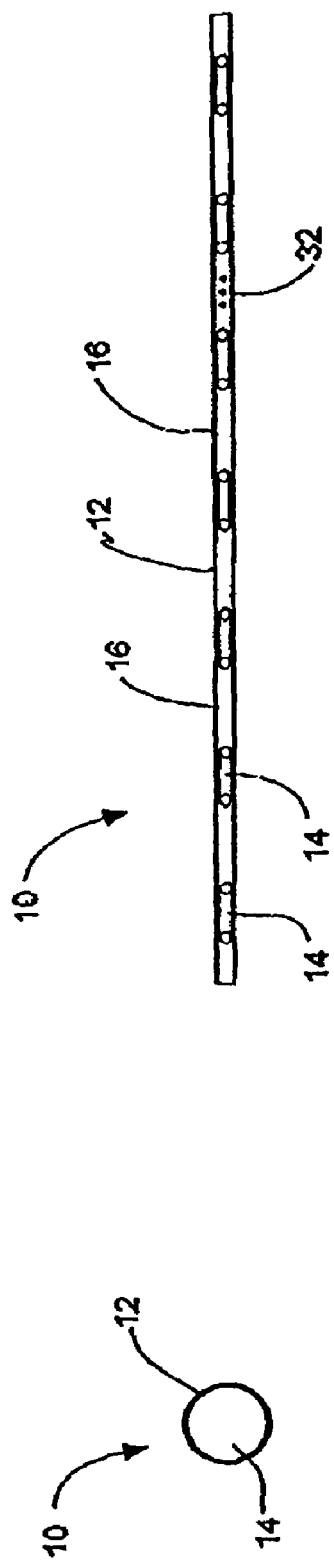
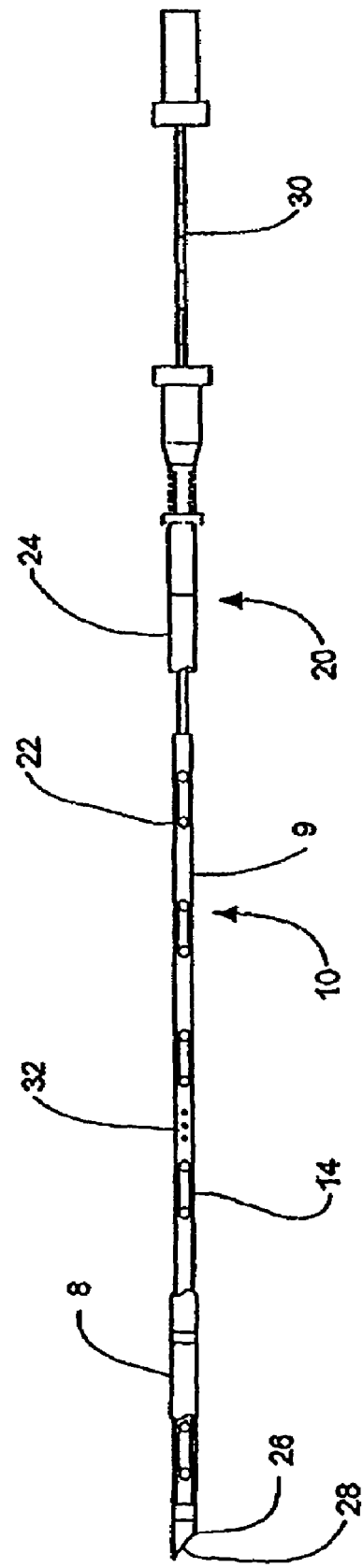
FIG. - 1
FIG. - 2
FIG. - 3

STRAND WITH END PLUG

PRIORITY CLAIM

This application is a divisional of U.S. patent application Ser. No. 10/397,940, filed Mar. 26, 2003, which a continuation of U.S. patent application Ser. No. 10/035,083, filed Dec. 28, 2001, now U.S. Pat. No. 7,060,020, which claims priority under 35 U.S.C. 119(e) to U.S. Provisional Patent Application No. 60/336,329, filed Nov. 2, 2001. All of the above listed applications are incorporated herein by reference.

FIELD OF INVENTION

The present invention relates to systems and methods for delivering a plurality of radioactive sources to a treatment site.

BACKGROUND

In interstitial radiation therapy, one method for treating tumors is to permanently place small, radioactive seeds into the tumor site. This method is currently accomplished by one of the following two procedures: (a) loose seeds are implanted in the target tissue, and/or (b) seeds are contained within a woven or braided absorbable carrier such as braided suture material and implanted in the target tissue. The loose seeds, however, are dependent on the tissue itself to hold each individual seed in place during treatment, and the woven or braided sutures do not assist in the placement of the seeds relative to the target tissue.

There have been many developments in brachytherapy (i.e. therapy relating to treating malignant tumors for handling such radioactive seeds). In one technique, hollow metal needles are inserted into the tumor and the seeds are thereafter inserted into the needles, while the needles are being retracted to deposit the seeds in the tumor. Such devices are shown in U.S. Pat. No. 4,402,308 which is incorporated herein by reference. The most commonly used instruments are the Henschke and Mick devices. The use of such devices has distinct disadvantages. The overall length of such devices is over 20 cm and such devices have significant weight making them difficult to manipulate.

Another disadvantage of the above technique is that the seeds are deposited in a track made by the needle. When the needle is withdrawn, there is a tendency for the seeds to migrate in that track resulting in a poor distribution of the seeds. Because the energy levels are low, distribution between centers of adjacent seeds should be on the order of about 1 cm for certain treatments. Poor distribution of seeds can result in undesirable concentrations of seeds resulting in either an over-dosage or under-dosage of radiation. Further, over time, the seeds tend to migrate along the needle track, away from the tumor, and accordingly patients commonly must repeat the procedure within a couple months to have seeds re-implanted near the tumor.

Further complicating the procedure is the fact that the seeds are small, because they need to fit in small bore needles to prevent excessive tissue damage. Due to their small size and high seed surface dose, the seeds are difficult to handle and to label, and can easily be lost. In addition, the technique of implantation of individual seeds is time consuming.

One preferred method of introducing seeds into the tumor site is using a pre-manufactured elongated assembly or implant that contains seeds spaced at 1 cm increments. This assembly is capable of being loaded into an introducer needle just prior to the procedure. What is desired in using an elongated assembly of seeds and spacers is the ability to insert such an assembly into a tumor site to provide controlled and precise placement of the radioactive seeds.

While assemblies with bio-absorbable materials and spaced radioactive seeds are known for use as interstitial implants, such assemblies are not entirely satisfactory. In one instance, the elongated implant is made using a bio-absorbable material consisting of an Ethicon Vicryl.RTM. This material is commonly known as PGA. Radioactive seeds and teflon spacers are inserted into the material. Needles loaded with the seeds in the carrier bio-absorbable material are sterilized or autoclaved causing contraction of the carrier material and resulting in a rigid column of seeds and spacers. This technique was reported in "Ultrasonically Guided Transperineal Seed Implantation of the Prostate: Modification of the Technique and Qualitative Assessment of Implants" by Van't Riet, et al., *International Journal of Radiation Oncology, Biology and Physics,* Vol. 24, No. 3, pp. 555–558, 1992 which is incorporated herein by reference. Such rigid implants have many drawbacks, including not having the ability to flex with the tissue over the time that the bio-absorbable material dissolves.

As the tissue or glands shrink back to pre-operative size, and thus as the tissue recedes, a rigid elongated implant does not move with the tissue, but remains stationary relative to the patient. The final location relative to the tumor is thus not maintained and the dosage of the radioactive seeds does not meet the preoperative therapy plan.

Another system for providing an elongated implant having radioactive seeds disposed therein is disclosed in U.S. Pat. No. 4,697,575 which is incorporated herein by reference. In this reference, a plurality of encapsulated radioactive seeds are positioned in a predetermined array. The seeds are encapsulated in individual capsules, with each capsule having a projection on one capsule end and a complementary recess on the remaining capsule end. A projection in one capsule is engageable with a recess in an adjacent capsule such that the desired number of seeds can be plugged together to form a column of rigid, bio-absorbable and elongated material. This implant is not entirely satisfactory inasmuch as it is time consuming and inefficient to carry out the manipulative steps of assembling such a strand of elongated material. Further the implant is quite rigid as it is inserted into a patient without the use of an introduction needle, as the implant itself acts as a rigid needle that is undesirably left in place.

In another embodiment disclosed in the above patent, a rigid needle implant containing radioactive segments, with break points, is inserted into the tumor. The needle implant is made of a bio-absorbable polymer that is rigid enough to be driven into the tumor without deflection and without the use of a separate hollow needle. When the proper depth is reached with the rigid polymer needle, the remaining, uninserted portion of the needle is broken off. This embodiment has the disadvantage of the above embodiment, in that being too rigid, the implant does not follow the tumor as it shrinks back to its normal size.

In U.S. Pat. No. 6,163,947, Coniglione, issued Dec. 26, 2000, and incorporated herein by reference, a string of hollow seeds described in U.S. Pat. No. 5,713,828, issued Feb. 3, 1998, also incorporated herein by reference, are strung onto a thin strand of suture material to form an array of seeds. This string of seeds is delivered into the tumor site placed within a hollow needle. Since the hollow lumen of the seeds are substantially smaller in diameter in relation to the outside diameter of the seed body, the string of suture material must be substantially smaller in diameter than the seeds themselves. The resulting diameter of the suture makes the suture axially weak and the suture can fold up between the seeds within the needle lumen as pressure is applied on the proximal end of the strand within the needle. Thus the difference in diameter between the seed and the thin suture material makes the assembly susceptible to collapse from axial force applied on the proximal end, resulting in jamming of the assembly within the needle lumen and/or the assembly not maintaining the proper desired spacing between radioactive seeds as the assembly is expelled into the treatment site.

One relevant reference discloses modification of the needle structure to include a reloadable cartridge. In such reference the needle is inserted and as a cartridge of seeds is emptied, the plunger of the device is withdrawn and a new cartridge containing radioactive seeds is loaded into the syringe (Moore, U.S. Pat. No. 4,086,914, issued May 2, 1978). Another reference offers a device for implanting individual seeds in a planar dispensing device with multiple needles to ensure accurate placement of the seeds relative to one another and the treatment site (Kirsch, U.S. Pat. No. 4,167,179, issued Sep. 11, 1979). Another reference disclosed a shielding devices for bead strands which prevents radiation exposure for health care personnel performing treatment with the radioactive seeds (Windarski, U.S. Pat. No. 4,509,506 issued Apr. 9, 1985). All of the above references are incorporated herein by reference.

In another technique for treating tumors disclosed in U.S. Pat. No. 5,460,592, and incorporated herein by reference, seeds are held in a woven or braided bio-absorbable carrier such as a braided suture. The carrier with the seeds laced therein is then secured in place to form a suitable implant. This braided assembly exhibits many drawbacks, such as when the braided assembly is placed into the tumor. The needle that carries the braided assembly must be blocked at the distal end to prevent body fluids from entering the lumen. If body fluid reaches the braided assembly while the assembly is still in the lumen of the needle, the braided assembly can swell and jam in the lumen. Because the assembly is made of a braided tubular material, it is difficult to push the assembly out of the needle. As the needle is withdrawn from the tumor, pressure on the proximal end of the braided assembly causes the braid to expand and jam inside the lumen of the needle. Finally, if the braided strand is successfully expelled from the needle, the relative spacing of the seeds may not be maintained, if the braided material has collapsed.

Other references that address such implants and materials include the following, all of which are incorporated herein by reference.

1. U.S. Pat. No. 1,578,945, issued January 1923 to Withers;

2. U.S. Pat. No. 2,067,589, issued January 1937 to Antrim;

3. U.S. Pat. No. 3,351,049, issued November 1967 to Lawrence;

4. Medi-Physics brochure entitled AI-125 Seeds.RTM. In Carrier,@ Model No. 6720;

5. Medi-Physics brochure entitled AI-125 Seed.RTM. Source Model 6711;" and

6. Martinez et al., *Int. J. Radiation Oncology Biol. Phys.,* Vol. 5, No. 3, March 1979, pp. 411–413.

SUMMARY OF SOME ASPECTS OF THE INVENTION

Accordingly, the present invention cures and addresses the disadvantages exhibited in the prior art devices and implants. What is desired is to provide a bio-absorbable carrier material having seeds disposed within the material, with the seeds being accurately spaced a predetermined distance from one another, with the seeds repeatably maintaining that spacing, even after being introduced into the body.

It is further desired that an elongated member with seeds be sufficiently rigid axially to allow expulsion of the member while maintaining the spacing between seeds, and that the member be flexible and pliable enough to move with the tissue as the tissue shrinks back to pre-operative size.

Accordingly, some of the objectives of the present invention include providing an elongated member with seeds dispersed throughout, which obviates the aforementioned disadvantages and allows placement of the seeds in accurate positions to provide the desired interstitial radiation dose to the location derived from a preoperative dosimeter plan.

A further object of the present invention is to provide a delivery system for interstitial radiation therapy, which is faster and easier to use than prior art systems.

Another object of the present invention is a delivery system that causes a minimum of trauma to tissue.

Yet another object of the present invention is a delivery system that allows for control of the radiation dosage given the tissue. Still further objects of the present invention are a delivery system that can be used and placed with precision, and that maintains the position of the implant after the implantation, until the bio-compatible material dissolves and the seeds have become inert. In another aspect the bio-compatible material is selected to absorb about when the half-life of the radioactive seeds is reached.

A further aspect is to have the implant be echogenic.

In accordance with an embodiment of the invention, the delivery system comprises a substantially axially stiff and longitudinally flexible elongated member that is bio-absorbable in living tissue. The member has a length that greatly exceeds its width or diameter. The elongated member has a plurality of radioactive seeds dispersed therein in a predetermined array.

In another embodiment, the substantially axially stiff and longitudinally flexible elongated member comprises a single continuous monofilament element of bio-compatible material that has a plurality of seed sources molded therein. The bio-compatible material can be preferably a bio-absorbable polymer or copolymer material that encapsulates the plurality of radioactive seeds.

A further embodiment of the invention is characterized as a substantially constant diameter solid elongated matrix member of a bio-absorbable polymer with seeds positioned therein at predetermined spacing along its length, whose diameter is a close fit to the needle lumen, thus preventing collapse as axial force is applied on the proximal end of the elongated matrix member. The space between the seed sources is maintained throughout the insertion and expulsion of the elongated matrix member. The diameter of the polymer between the seeds may be slightly reduced in diameter in relation to the overall diameter of the elongated matrix member, but is of sufficient diameter so as to not allow collapse of the matrix member within the needle lumen.

The present embodiment of the invention further allows for variation in any spacing between seeds, as the semi-rigid, deflecting elongate member could be produced under a doctor=s prescription for each patient, with optimal seed distribution for a particular patient=s treatment program.

This one object of the invention is to provide an implant that can be custom made as specified by a prescription for an individual patient.

Further aspects, objects, advantage and embodiment of the invention can be understood from the specification, the figures and the claims.

DESCRIPTION OF THE DRAWINGS

FIG. 1 is an enlarged side view of an embodiment of the therapeutic implant of the invention.

FIG. 2 is an enlarged view of a cross section of an embodiment of the therapeutic implant of the invention of FIG. 1.

FIG. 3 is an enlarged side view of the brachytherapy device including the implant of FIG. 1.

DETAILED DESCRIPTION OF THE PREFERRED EMBODIMENTS

In accordance with an embodiment of the invention, a substantially axially, semi-rigid and longitudinally flexible elongated member made of material, which is bio-absorbable in living tissue, is provided for insertion in tumors. A plurality of radioactive seeds are encapsulated and positioned in a predetermined array in the member in the desired spaced relationships.

The seeds can be of various types having low energy and low half-life such as Iodine seeds, known as I-125 seeds, consisting of a welded titanium capsule containing iodine 125 absorbed on a silver rod, or Palladium 103 seeds. Examples of radioactive seeds used to manufacture the therapeutic element appear in Table 1 below.

TABLE 1

Seed Manufacturers and Common Types of Seeds.

| PART NUMBER | MANUFACTURER | SEED NAME |
|---|---|---|
| IODINE[125] | | |
| 80040-A | Amersham 6702 | OncoSeed |
| 80040-B | Amersham 6711 | RAPID Strand |
| 80040-C | North American Scientific | IoGold |
| 80040-D | Best Industries | BEST Iodine-125 |
| 80040-E | Bebig | Symmetra |
| 80040-F | Mills Biopharmaceuticals | ProstaSeed |
| 80040-G | Syncor | PharmaSeed |
| 80040-H | International Isotopes | IsoStar |
| 80040-I | Implant Sciences | I-Plant |
| 80040-J | International Brachytherapy | InterSource-125 |
| 80040-K | Source Tech | STM1251 |
| 80040-L | DRAXIMAGE, Inc. | BrachySeed |
| PALLADIUM[103] | | |
| 80035-A | North American Scientific | Pd Gold |
| 80035-B | Theragenics | Theraseed 200 |
| 80035-C | Best Industries | BEST Palladium-103 |
| 80035-D | International Brachytherapy | InterSource 103 |

Additionally, seeds can be manufactured using iridium 192, cesium 131, gold 198, yttrium 90 and phosphorus 32. Further radioactive isotopes used to manufacture seeds are not limited to these examples, but can include other sources of different types of radiation. In addition, it is to be understood that other types of seeds can be used. In particular, seeds such as those described in U.S. Pat. No. 6,248,057, which patent is incorporated herein by reference and which is entitled AAbsorbable Brachytherapy and Chemotherapy Delivery Devices and Methods,@ can be used with the present invention. These seeds include radiation delivery devices, drug delivery devices, and combinations of radiation and drug delivery devices in the form of beads, seeds, particles, rods, gels, and the like. These particular seeds are absorbable wherein the radiation element or drug delivery element is contained within, for example, absorbable polymers such as those listed below or in the above-referenced patent. In such seeds, the bio-absorbable structure can have a predefined persistence which is the same as or substantially longer than a half life of the radioactive element contained in the bio-absorbable structure. These above bio-absorbable seeds can be used in the same manner as the seeds described herein with respect to the invention.

The substantially axially, semi-rigid, and longitudinally flexible elongated member may be made of any of the natural and/or synthetic bio-compatible and bio-absorbable materials. Natural and synthetic polymers and copolymers can be used. Examples of synthetic bio-absorbable polymer materials are the polymers and copolymers of glycolide and lactide, polydioxanone and the like. Such polymeric materials are more fully described in U.S. Pat. Nos. 3,565,869, 3,636,956, 4,052,988 and European Patent Application No. 30822, all of which are incorporated herein by reference. Specific examples of bio-absorbable polymeric materials that can be used to produce the substantially axially stiff and longitudinally flexible elongated member of an embodiment of the present invention are polymers made by ETHICON, Inc., Somerville, N.J., under the trademarks "MONOCRYL" (polyglycoprone 25) and "MAXON" (Glycolide and Trimethylene Carbonate), which material is incorporated herein by reference.

Table 2 below provides examples of polymers (and manufacturers) suitable for use in producing embodiments the therapeutic member of the invention. A further discussion of such biodegradable polymers can be found in an article by John C. Middleton and Arthur J. Tipton entitled "Synthetic Biodegradable Polymers as Medical Devices,@ published March 1998 in *Medical Plastics and Bio-materials,* which article is incorporated herein by reference.

TABLE 2

Biodegradable polymers, properties and degradation time.

| POLYMER | MELTING POINT (□C) | GLASS-TRANSITION TEMP (□C) | MODULUS (Gpa)[a] | DEGRADATION TIME (MONTHS)[b] |
|---|---|---|---|---|
| PGA | 225–230 | 35–40 | 7.0 | 6 to 12 |
| LPLA | 173–178 | 60–65 | 2.7 | >24 |
| DLPLA | Amorphous | 55–60 | 1.9 | 12 to 16 |
| PCL | 58–63 | (−65)–(−60) | 0.4 | >24 |
| PDO | N/A | (−10)–0 | 1.5 | 6 to 12 |
| PGA-TMC | N/A | N/A | 2.4 | 6 to 12 |
| 85/15 DLPLG | Amorphous | 50–55 | 2.0 | 5 to 6 |
| 75/25 DLPLG | Amorphous | 50–55 | 2.0 | 4 to 5 |
| 65/35 DLPLG | Amorphous | 45–50 | 2.0 | 3 to 4 |
| 50/50 DLPLG | Amorphous | 45–50 | 2.0 | 1 to 2 |

[a]Tensile or flexural modulus.
[b]Time to complete mass loss. Rate also depends on part geometry.

The final hardness of the polymer of elongate member should preferably be in a range from 20 to 80 durometers, and, more preferably, in the range of 20–40 durometers. The bio-absorbable material should preferably be absorbed in living tissue in a period of time of from about 70 to about 120 days, but can be manufactured to be absorbed anywhere in a range from 1 week to 1 year, depending on the therapeutic plan for each specific patient. Preferably, the bio-absorbable material is selected to absorb about when the half-life of the radioactive seeds is reached.

The member or strand is fashioned with a manufacturing method known as insert or compression molding. The radioactive seeds are placed into a fixture that spaces the seeds at the appropriate intervals in a cavity that is shaped to the desired final dimensions of the elongated member. All the spacings can be of different lengths, if the preoperative therapeutic plan so specifies. The synthetic polymer is introduced into the mold at a temperature that is above the melt point of the polymer. The polymer flows around the seeds within the cavity, surrounds the seeds and fills in the spaces between the seeds. After the mold has cooled, it is disassembled, and the finished elongated member is removed. Because the polymer flows at temperatures significantly greater than 250□ F, the therapeutic element can easily be steam sterilized before implantation.

As specified above, the elongated member encapsulating radioactive seeds may be fashioned using compression molding techniques. Compression molding forms the molded piece in a two part mold where the polymer material is placed within the cavities of the mold in a liquid state. The seeds are placed in position within the cavities filled with the polymer and the mold is closed and compressed, then cooled to form a piece that conforms to the shape of the closed cavity.

The manufacturing process also can make the member echogenic. In the case of the molding of the elongated member, air can be entrapped in the polymer material. During the cooling stage of the molding process, the mold is placed in a vacuum chamber and the air in the chamber is evacuated. This causes the entrapped air in the mold to come out of solution from the polymer, and as the mold cools, this air is entrapped within the cooling polymer in the form of minute bubbles suspended in the plastic.

Air is a strong reflector of ultrasound energy, since the inherent impedance of air is many times greater than body tissue. When the elongated member is introduced into the body and imaged with ultrasound, the elongated member is clearly visible in the resulting image, and is, thus, echogenic.

The resulting elongated member is now a single solid monofilament of the polymer with the seeds spaced within the monofilament and encapsulated at the appropriate intervals. The member is generally very axially flexible such that it can be bent back upon itself in a circle without kinking. However, the member has sufficient column strength along its longitudinal axis so that the member can be urged out of a hollow needle without the member folding upon itself. Again, the intervals can be selected to be any distance or combination of distances that are optimal for the treatment plan of the patient.

In FIG. 1, the therapeutic elongated element or member or matrix or strand 10 is displayed having the semi-rigid, radially flexible polymer 12 and the radioactive seeds 14. As can be seen in FIG. 1, the polymer fills the spacing segments 16 in a contiguous manner to fashion the total elongate member.

FIG. 3 shows a side view of the brachytherapy device 20. The needle 22 is shown partially broken away and has a sheath component 24, and is loaded with the therapeutic element or member 10. The beveled end 26 of the needle 22 is plugged with a bio-compatible substance 28. The plug prevents fluids and tissue from entering the needle and coming in contact with the member 10 prior to the placement of the member or strand 10 adjacent the tumor. The plug 28 can be made out of a bone wax or can be made of one of the bio-absorbable polymers or copolymers listed herein. Further, the plug can be the end of the member or strand 10 that is heated and reflowed after the strand or member is inserted into the needle. A stylet or stylus 30 is inserted into the needle until it meets the therapeutic element or member 10. Then, the needle 22 is inserted into the site and the therapeutic member 10 is gradually extruded from the needle via the static force of the stationary stylus 30, as the needle 22 is pulled back.

Based on the above, it is evident that the present invention provides for an embodiment having an elongated member which is comprised of a biodegradable polymer which encapsulates a plurality of spaced radioactive therapeutic seeds. The seeds can be spaced in custom manner so that each member or strand is designed for the particular patient. That is to say that the spacing between each seed pair in a strand or member can be different for each seed pair. Further, each individual strand can have an entirely different seed spacing pattern than the next strand or member. Characteristically, or typically, for a surgical procedure, up to twenty-five of such strands or members are used to encircle the organ or tumor that is affected.

Further, such an arrangement provides for a strand or member that is stiff along its longitudinal axis. That is to say that the strand or member has column strength or stiffness while the strand or member is flexible in the direction which is radial or substantially perpendicular to the longitudinal axis. Accordingly the strand or member in a preferred embodiment is able to bend back upon and touch itself, when formed in a characteristic length.

In other embodiments, the strand or member can be made with the incorporation of drugs and/or hormones and/or other therapeutics which are embedded in or formed in the polymer and/or seeds. Thus, the embodiment of the invention can deliver not only radioactive seeds, but such therapeutic drugs, hormones and other therapeutic devices. In addition, the strand or member can deliver heated seeds such as provided by ATI Medical. These seeds can be preferably heated to from about six (6) degrees centigrade to about seventy (70) degrees centigrade prior to being inserted into a patient in a preferred embodiment.

It should be understood that other seed types can be used with the present invention. Thus, for example, in addition to the above encapsulated seeds, seeds which are made of radioactive or coiled wires can be embedded in the polymer and be within the spirit and scope of the invention. These seeds can be individual seeds which are spaced within a polymer or a continuous seed which extends the length of the strand or member.

Further to the invention, as discussed above, it should be understood that the strand or member can be made echogenic by the incorporation of, for example, air bubbles 32 in the polymer spaces between the seeds, as can be seen in FIGS. 1 and 3. These air bubbles or pockets can be formed in the polymer in ways identified above and other ways known to one of skill in the art.

According to the above, the advantages of the improved delivery system submitted of the present invention are:

1. The substantially axially stiff and longitudinally flexible elongated member allows controlled placement of the plurality of radioactive seeds that are encapsulated and positioned in a predetermined array in the member without migration of the individual radioactive seeds during the time the seeds are treating the tumor.

2. The fixed linear positioning of the seeds minimizes "hot" and "cold" radiation spots due to undesirable movement of the seeds.

3. The normal tissue is spaced away from the seed surface by the thickness of the body of polymer, to decrease necrosis from a high local dose.

4. The axial stiffness of the elongated member allows the elongated member to be urged out of the needle as the needle is withdrawn, without the member jamming in the needle, by collapsing or expanding as the needle is withdrawn from the tumor site.

5. The longitudinal flexibility of the elongated member allows locational accuracy to be maintained as the gland shrinks to pre-procedural size, as the swelling that occurs during tissue disruption and needle manipulation recedes.

6. Increased speed of implant resulting in reduced surgical time and health care provider radiation exposure.

Method of Delivering Customized Strands and/or Members Per a Therapeutic Prescription:

As is known in the industry, there is software which can be used to provide brachytherapy treatment planning guides which are customized for each individual patient. Such software is provided by Rossmed which is located at Ross Medical, 7100 Columbia Gateway Drive, Suite 160, Columbia, Md. 21046. This particular software, which is incorporated herein by reference, is known as the Strata suite, which software helps physicians to develop and visualize low dose rate brachytherapy treatment plans for treating malignant tumors in human tissue. The treatments entail the use of radioactive seed sources which are implanted adjacent to the malignant tissue. The Strata software uses imaging to create a three-dimensional reconstruction of the patient's anatomy. The software is able to plan the placement of the seeds within the target. The radiation dose that is delivered to the target can be computerized and visualized using the software. The software can then specify an optimal number of strands or members along with optimal seed dosages and spaces between seeds. At times, the loading plans so specified cannot be optimized by the physician in preparing the seed and spacer loads for the needles, as the spacers come in only predefined lengths.

Accordingly, with the present invention, the software can be used to prepare a prescription which optimizes the number of members or strands, and placement and spacing of seeds for each of the strands or members. This optimization plan can then be sent to a manufacturing site. By using the techniques of an embodiment of the present invention, an optimized strand or member can be created with the specified number of seeds and the specified distances between each seed pair. Once this prescription is filled at the manufacturing site, the custom strand or member can be sent back to the physician for treatment of the patient. With such an arrangement, radiation patterns can be optimally established for the treatment of each patient. Further, the preparation time for the physician is greatly diminished as the physician does not have to hand assemble and hand load the seeds and spacers into the needle.

Further, even if the physician were to use a prescription provided by the above software, with prior manufacturing techniques, the physician would only receive from the manufacturing facility a strand or member which has seeds spaced at predefined intervals, which are the lengths or the pre-manufactured spacers. Accordingly, optimal treatment as provided by the custom strands or members manufactured according to the present invention could not be realized.

Additional aspects, objects and advantages of the invention can be obtained through a review of the appendant claims and figures. It is to be understood that other embodiments can be fabricated and come within the spirit and scope of the claims and the invention.

What is claimed is:

1. A treatment strand for insertion into a patient using a needle, the strand comprising:
   an elongated member having first and second longitudinal ends; and
   a plurality of treatments seeds within said elongated member between said longitudinal ends;
   wherein one of said longitudinal ends of said elongated member is a needle plug that is configured to prevent at least one of fluid and tissue from entering a needle when said elongated member is loaded into a needle and the needle is initially inserted into a patient.

2. The treatment strand of claim 1, wherein said elongated member and said needle plug are made of a bio-absorbable material.

3. The treatment strand of claim 1, wherein said elongated member and said needle plug are made from a same bio-absorbable material.

4. The treatment strand of claim 1, wherein said needle plug is a heated and reflowed one of said longitudinal ends of said elongated member.

5. The treatment strand of claim 4, wherein said needle plug is made from a bio-absorbable material.

6. The treatment strand of claim 1, wherein said seeds are spaced apart from one another in accordance with a prescription treatment plan.

7. A treatment strand for insertion into a patient using a needle, the strand comprising:
   an elongated member;
   a plurality of treatments seeds molded within said elongated member; and
   a needle plug that is a longitudinal end of said elongated member, wherein said needle plug is configured to prevent at least one of fluid and tissue from entering a needle when said elongated member is loaded into a needle and the needle is initially inserted into a patient.

8. The treatment strand of claim 7, wherein said plurality of treatment seeds comprise a plurality of radioactive treatment seeds.

9. The treatment strand of claim 8, wherein said elongated member and said needle plug are made of a bio-absorbable material.

10. The treatment strand of claim 7, wherein said elongated member and said needle plug are made from a same bio-absorbable material.

11. The treatment strand of claim 7, wherein said needle plug is a heated and reflowed end of said elongated member.

12. A method for making a device for use in interstitial radiation therapy, comprising:
   (a) creating an elongated member with first and second longitudinal ends and a plurality of treatments seeds within said elongated member between said longitudinal ends; and
   (b) transforming one of said longitudinal ends of said elongate member into a needle plug.

13. The method of claim 12, wherein step (b) comprises heating and reflowing said one of said longitudinal ends of said elongated member to thereby transform said one of said longitudinal ends into said needle plug.

14. A method for making a device for use in interstitial radiation therapy, comprising:

(a) creating an elongated member with first and second longitudinal ends and a plurality of treatments seeds within said elongated member between said longitudinal ends; and (b) creating a needle plug at one of said longitudinal ends of said elongated member by heating one of said longitudinal ends of said elongated member to create said needle plug.

15. The method of claim 12, wherein said needle plug is configured to prevent at least one of fluid and tissue from entering a needle when said elongated member is loaded into a needle and the needle is initially inserted into a patient.

16. A method for making a device for use in interstitial radiation therapy, comprising:

(a) creating an elongated member with first and second longitudinal ends and a plurality of treatments seeds within said elongated member between said longitudinal ends;

(b) inserting said elongated member into a needle; and (c) creating a needle plug at one of said longitudinal ends of said elongated member by heating one of said longitudinal ends of said elongated member after said elongated member is inserted into the needle.

17. The method of claim 12, wherein step (a) comprises creating said elongated member from a bioabsorbable material.

18. A method for providing a device for use in interstitial radiation therapy, comprising:

(a) providing an elongated member with first and second longitudinal ends and a plurality of treatments seeds within said elongated member between said longitudinal ends; and (b) heating one of said longitudinal ends of said elongated member to create a needle plug that prevents at least one of fluid and tissue from entering a needle when said elongated member is loaded into a needle and the needle is initially inserted into a patient.

19. A method for providing a device for use in interstitial radiation therapy, comprising:

(a) providing an elongated member with first and second longitudinal ends and a plurality of treatments seeds within said elongated member between said longitudinal ends;

(b) inserting said elongated member into a needle; and (c) after said elongated member is inserted into the needle, heating one of said longitudinal ends of said elongate member to create a needle plug that prevents at least one of fluid and tissue from entering the needle when the needle is initially inserted into a patient.

* * * * *